United States Patent
Ko et al.

(10) Patent No.: US 7,569,238 B2
(45) Date of Patent: Aug. 4, 2009

(54) ANTITUSSIVE AGENT AND METHOD FOR MAKING THE SAME

(75) Inventors: Feng-Nien Ko, Taipei (TW); Wei-Ja Wang, Taipei (TW); Cheng-Ko Liu, Shindian (TW); Pin-Fen Chen, Taipei (TW); Yu-Feng Han, Taichung (TW); Mai-Yu Lee, Taipei (TW)

(73) Assignee: Pharmaceutical Industry Technology and Development Center, Taipei Hsien (TW)

( * ) Notice: Subject to any disclaimer, the term of this patent is extended or adjusted under 35 U.S.C. 154(b) by 334 days.

(21) Appl. No.: 10/423,966

(22) Filed: Apr. 28, 2003

(65) Prior Publication Data

US 2004/0213863 A1 Oct. 28, 2004

(51) Int. Cl.
*A61K 36/00* (2006.01)
(52) U.S. Cl. ........................ 424/773; 424/725
(58) Field of Classification Search ................. 424/725; 514/850
See application file for complete search history.

(56) References Cited

FOREIGN PATENT DOCUMENTS

CN 1200928 A * 12/1998

OTHER PUBLICATIONS

K. Y. Lee, S. H. Sung, Y. C. Kim. New Acetylcholinesterase-Inhitbitory Pregnane Glycosides of Cynanchum atratum Roots, Helv. Chim. Acta, 86:474-483 (2003).* http://v3.espacenet.com/textdoc?DB=EPODOC&IDX=CN1253792&F=0.*
http://web.archive.org/web/20021108040254/http://www.herbasin.com/database/baiwei.htm (Accessed Jan. 28, 2006).*
Lin, C-C; Yen, M-H,; Wu, Y-W; Xu, G-J. Amer. J. Chinese Med., 1995, XXIII (3-4), 305-312.*
Zhang, Z-X; Zhou, J; Hayashi, K.; Mitsuhashi, H. Chem. Pharm. Bull. 1985; 33(4): 1507-1514.*
Liang et al. 'Pharmacological comparative study on baiqian and baiwei', Zhongguo Zhong Yao Za Zhi, vol. 21, No. 10 (1996) 622-625, PubMed Abstract only.*
http://web.archive.org/web/20021108040254/http://www.herbasin.com/database/baiwei.htm (Accessed Jan. 28, 2006).*
Lin, C-C; Yen, M-H,; Wu, Y-W; Xu, G-J. Amer. J. Chinese Med., 1995, XXIII (3-4), 305-312.*
Zhang, Z-X; Zhou, J; Hayashi, K.; Mitsuhashi, H. Chem. Pharm. Bull. 1985; 33(4): 1507-1514.*
Day et al. (J. Nat. Products (2002), vol. 64, pp. 608-611).*
Helvetica Chimica Acta (Feb. 2003), vol. 86, Table of Contents.*

* cited by examiner

*Primary Examiner*—Susan C Hoffman
(74) *Attorney, Agent, or Firm*—Fei-Fei Chao; Andrews Kurth, LLP

(57) ABSTRACT

An antitussive agent. A composition for relieving, preventing and/or treating cough includes a sufficient amount of Cynanchi Atrati Radix extract as an active component. The effective Cynanchi Atrati Radix extract is prepared by extracting Cynanchi Atrati Radix with water, ethanol, hexane, ethyl acetate or a combination thereof. The crude extract can be further fractioned by ultrafiltration or reverse phase column.

12 Claims, No Drawings

ANTITUSSIVE AGENT AND METHOD FOR MAKING THE SAME

BACKGROUND OF THE INVENTION

1. Field of the Invention

The present invention relates to a pharmaceutical composition, and, in particular, to an antitussive agent containing Cynanchi Atrati extract as an active antitussive component and the method for making the same.

2. Description of the Related Art

It should be noted that reference is made herein to concepts and practices well known within the established realm of traditional Chinese herbal remedy. A brief notation regarding the pertinent aspects of the art appears in Appendix A.

Cynanchi Atrati Radix is the root and rhizome of *Cynanchum atratum* Bunge or *C. versicolor* Bunge, family Asclepiadaceae, which is known as Bai Wei (rendered herein in accordance with pinyin standards of Chinese Romanization) in traditional Chinese medicine.

Crude drugs of Cynanchi Atrati Radix used in Chinese medicine are generally horse's tail-shaped, 10-15 cm long with rhizome stout, tubercular, transversely growing and circular stem tracing at the upper part with numerous slender roots clustered in the lower regions, The root of Cynanchi Atrati is 0.1-0.2 cm in diameter, grey-yellow and fragile. Crude drugs of Cynanchi Atrati Radix are conventionally prepared as bitter and salty segments, characterized within the parameters of traditional Chinese herbal remedies as being cold in nature and attributive to stomach and liver channels.

In traditional Chinese medicine, Cynanchi Atrati Radix is known as a successful remedy for lower asthenic fever. Specifically, Cynanchi Atrati Radix is regarded as curative for seasonal febrile disease involving depleted yin levels with prolonged fever or high fever at night subsiding in the morning, infantile summer fever, postpartum fever, and so on. Traditional indications for Cynanchi Atrati Radix disperse the disruptive factors from the body surface, for common cold with prolonged fever, especially those with yin-deficiency. Promote diuresis and relieve stranguria of heat type and when complicated by hematuria.

In addition, Cynanchi Atrati Radix is prescribed conventionally in combination with Cortex Lycii Radicts or di gu pi (rendered herein in accordance with pinyin standards of Chinese Romanization) or Herba Artemisiae Annuae in Chinese herbal medicine.

SUMMARY OF THE INVENTION

An object of the invention is to provide an antitussive agent that comprises an extract of Cynanchi Atrati Radix.

The present invention also provides a pharmaceutical composition containing the antitussive agent and a pharmaceutical acceptable carrier and/or excipient.

Another object of the invention is to provide a method for preparing the antitussive agent, and a method for relieving and/or preventing cough in mammals.

In an embodiment, the Cynanchi Atrati extract is prepared by extracting Cynanchi Atrati Radix, such as *Cynanchum atratum* Bunge or *C. versicolor* Bunge, with water, ethanol, hexane, ethyl acetate or a combination thereof. Moreover, the crude extract is preferably filtered by an ultrafiltration membrane with a molecular weight cut off 1000 to 3000 daltons to obtain a filtrate as an active component of the antitussive agent.

In addition, the crude extract of Cynanchi Atrati Radix can further be loaded onto a reverse phase column packed with HP20 resin or RP-18 resin and eluted with water and 80-95% ethanol solution sequentially. The ethanol eluate is collected as an active component of the antitussive agent.

In a preferred embodiment, the crude extract of Cynanchi Atrati Radix, with or without filtration using an ultrafiltration membrane, is further loaded onto a reverse phase column and then eluted with water and 80-95% ethanol solution sequentially. The ethanol eluate is collected and concentrated approximately 50 times. Water is added to the concentrated ethanol eluate to give a concentration of 5-20 mg dry basis/ml and then concentrated approximately 10 times. The eluate is then filtered to obtain a filtrate as the extract of Cynanchi Atrati Radix.

DETAILED DESCRIPTION OF THE INVENTION

Evaluation Model

The antitussive activity of various extracts of Cynanchi Atrati Radix is herein evaluated according to the method described by Winter C. A. et al. (J. Pharmacol. Exp. Ther. 112:99, 1954) with modification.

Duncan Hartley derived male and female guinea pigs, weighing 450±50 g, were used. Each guinea pig was placed in a 4-liter sealed chamber equipped with an ultrasonic nebulizer to provide cough-inducing irritant by aerosol. A microphone was set to amplify coughing sounds from the guinea pigs. The animals were exposed to an aerosolized solution of 10% citric acid for 10 seconds and selected if 9-15 coughs ensued in the following 5 minutes. On the next day, solvent, i.e. distilled water, or extracts were administered orally to the animals twice a day (10:00 am and 4:00 pm). The animals were again exposed to aerosolized 10% citric acid 60 minutes after the second dose administration. The inhibition activity of extracts on citric acid-induced cough was evaluated as follows:

Inhibition (%)=[(Number of coughs before administration)−(Number of coughs after administration)]/(number of coughs before administration)× 100%

Sample Preparation and Antitussive Assessment Thereof

EXAMPLE 1

The dry rhizome of *Cynanchum atratum* was used. One kilogram pulverized dry material of *Cynanchum atratum* was heated to boil and refluxed twice with 10 L of the following solvents: water (Sample 1-1), 50% ethanol (Sample 1-2), 95% ethanol (Sample 1-3), ethyl acetate (EA) (Sample 1-4) and hexane (Sample 1-5), respectively. The extracts were then filtered with 350 mesh sieve and the filtrates were collected, respectively. The filtrates were further centrifuged continuously at 1089×g (Avanti™ J-25I, Beckman) for 3 hr to precipitate microparticles and impurities. The supernatants were further concentrated and freeze-dried. The antitussive assessment of the above extracts is shown in Table 1.

TABLE 1

| sample | Dosage (g/kg) | Inhibition rate* (%) |
|---|---|---|
| 1-1 | 1.0 | 62 ± 8 |
|  | 0.5 | 49 ± 8 |
| 1-2 | 1.0 | 78 ± 4 |

TABLE 1-continued

| sample | Dosage (g/kg) | Inhibition rate* (%) |
|---|---|---|
|  | 0.5 | 88 ± 7 |
| 1-3 | 1.0 | 75 ± 9 |
|  | 0.5 | 66 ± 5 |
| 1-4 | 1.0 | 88 ± 4 |
|  | 0.5 | 41 ± 6 |
| 1-5 | 1.0 | 74 ± 3 |
|  | 0.5 | 56 ± 4 |

*data are presented as means ± s.e. (N = 4)

The results in Table 1 show that water, 50% ethanol, 95% ethanol, ethyl acetate (EA) and hexane extracts of *Cynanchum atratum* inhibited at least 60% of citric acid-induced coughs in the guinea pigs at 1.0 g/kg dosage.

EXAMPLE 2

120 g of dried *Cynanchum atratum* was extracted with 50% ethanol as in Example 1. The 50% ethanol extract of *Cynanchum atratum* was concentrated to 500±100 mL and adjusted to a volume of 2 L with water. The 2 L extract was further filtered by way of an ultrafiltration membrane with molecular weight cut off 1,000 (Amicon LP-1, inlet P=1.5 kg/cm$^2$, outlet P=0.5 kg/cm$^2$). 1800 mL of the filtrate was firstly collected and 1800 mL water was added to the retentate to continue the ultrafiltration, repeating the process for 3 times. The retentate (Sample 2-1) with molecular weight greater than 1,000 dalton and the filtrate (Sample 2-2) containing substances with molecular weight less than 1,000 dalton were collected respectively and freeze-dried. The antitussive assessment of the above samples is shown in Table 2.

TABLE 2

| Sample | Dosage (g/kg) | Inhibition rate* (%) |
|---|---|---|
| 2-1 | 0.5 | 65 ± 8 |
| 2-2 | 0.5 | 57 ± 11 |

*data are presented as means ± s.e. (N = 4)

The results in Table 2 show that both of the fractions with molecular weight more and less than 1,000 dalton of the 50% ethanol extract of *Cynanchum atratum* are active to inhibit citric acid-induced coughs in the guinea pigs at 0.5 g/kg dosage.

EXAMPLE 3

680 g of dried *Cynanchum atratum* was extracted with water as in Example 1. 12000 g water extract obtained was further filtered by way of an ultrafiltration membrane with molecular weight cut off 1,000 (Amicon LP-1, inlet P=1.5 kg/cm$^2$, outlet P=0.5 kg/cm$^2$). 10800 g of the filtrate was firstly collected and 10800 g water was added to the retentate, repeating the process for 3 times. The filtrate containing substances with molecular weight less than 1,000 dalton was concentrated to 0.812 dry base g/mL. The concentrated filtrates containing 38.5 g and 31.5 g dry powder were loaded onto columns packed with 3080 g and 2520 g HP20 (Diaion, Mitsubishi Chemistry inc.) resin, respectively, i.e. in a ratio of 1 g filtrate/80 g HP20 resin. The columns were first eluted with 24640 g and 20160 g water, respectively and then eluted with 50% or 95% ethanol respectively. 24640 g of 50% ethanol eluate and 20160 g of 95% ethanol eluate were collected, respectively (Sample 3-1 and 3-2). The 50% ethanol eluate and the 95% ethanol eluate were concentrated and freeze-dried. The antitussive assessment of the above eluates is shown in Table 3.

TABLE 3

| Sample | Dosage (g/kg) | Inhibition rate* (%) |
|---|---|---|
| 3-1 | 1.0 | 71 ± 7 |
|  | 0.5 | 41 ± 9 |
| 3-2 | 1.0 | 43 ± 9 |
|  | 0.5 | 38 ± 11 |

*data are presented as means ± s.e. (N = 4)

The results in Table 3 show that Sample 3-1 is highly active to inhibit citric acid-induced coughs in the guinea pigs at 1.0 g/kg dosage.

EXAMPLE 4

1200 g of dried *Cynanchum atratum* was extracted with water as in Example 1. The water extract was further concentrated to a concentration of 0.59 g/ml. A concentrated water extract containing 170 g dry powder was further loaded onto a reverse phase column packed with 6800 g HP20 resin, in a ratio of 1 g dry basis of the extract/40 g resin, The column was first eluted with 68000 g water and then eluted with 95% ethanol. The water eluate and 68000 g 95% ethanol eluate were collected respectively (Sample 4-1 and 4-3), concentrated and freeze-dried.

Similarly, 760 g of dried *Cynanchum atratum* was extracted with water as in Example 1. The water extract was further concentrated to a concentration of 0.811 g/mL. A concentrated water extract containing 120 g dry powder was further loaded onto a reverse phase column packed with 9600 g HP20 resin, in a ratio of 1 g dry basis of the extract/80 g resin. The column was first eluted with 76800 g water and then eluted with 95% ethanol. The water eluate and 76800 g 95% ethanol eluate were collected respectively (Sample 4-2 and 4-4), concentrated and freeze-dried.

The antitussive assessment of the above eluates is shown in Table 4.

TABLE 4

| Sample | Dosage (g/kg) | Inhibition rate* (%) |
|---|---|---|
| 4-1 | 1.0 | 62 ± 8 |
| 4-2 | 1.0 | 15 ± 12 |
| 4-3 | 1.0 | 59 ± 10 |
| 4-4 | 1.0 | 72 ± 9 |

*data are presented as means ± s.e. (N = 4)

The results in Table 4 show that the eluates through the reverse phase column (Sample 4-1, 4-3 and 4-4) were active for reducing citric acid-induced coughs at 1.0 g/kg dosage, except for the water eluate of column packaged in the ratio of 1 g extract/80 g HP20 resin (Sample 4-2).

EXAMPLE 5

3000 g of dried *Cynanchum atratum* was extracted with water as in Example 1. Concentrated water extracts containing 345 g and 250 g dry powder were further loaded onto reverse phase columns packed with 6900 g and 5000 g HP20 resin, respectively, in a ratio of 1 g dry basis of the extract/20 g resin. The columns were first eluted with 75900 g and 60500 g water respectively and then eluted with 70% and 95% ethanol, respectively. The 75900 g 70% ethanol eluate and 60500 g 95% ethanol eluate were collected respectively (Sample 5-1, and 5-2), concentrated and freeze-dried.

Similarly, 1500 g of dried *Cynanchum atratum* was extracted with water as in Example 1. Concentrated water extracts containing 130 g and 115 g dry powder were further loaded onto reverse phase columns packed with 10400 g and 9200 g HP20 resin, respectively, in a ratio of 1 g dry basis of the extract/80 g resin. The columns were first eluted with 62400 g and 55200 g water, respectively and then eluted with 50% and 95% ethanol, respectively. The water eluate, 62400 g 50% ethanol eluate and 55200 g 95% ethanol eluate were collected respectively (Sample 5-3, 5-4 and 5-5), concentrated and freeze-dried.

Similarly, 3000 g of dried *Cynanchum atratum* was extracted with water as in Example 1. Concentrated water extracts containing 250 g and 210 g dry powder were further loaded onto reverse phase columns packed with 3750 g and 3150 g HP20 resin, respectively, in a ratio of 1 g dry basis of the extract/15 g resin. The columns were first eluted with 37500 g and 31500 g water, respectively and then eluted with 50% and 95% ethanol, respectively. 37500 g 50% ethanol eluate and 31500 g 95% ethanol eluate were collected respectively (Sample 5-6 and 5-7), concentrated and freeze-dried.

Samples 5-6 and 5-7 were further filtered by way of an ultrafiltration membrane with molecular weight cut off 1,000 (Amicon LP-1, inlet P=1.5 $kg/cm^2$, outlet P=0.5 $kg/cm^2$), respectively. 1800 mL of the filtrate was firstly collected and 1800 mL water was added to the retentate to continue the ultrafiltration, repeating the process for 3 times. The retentates containing substances with molecular weight more than 1,000 dalton (Samples 5-8 and 5-10) and the filtrates containing substances with molecular weight less than 1,000 dalton (Samples 5-9 and 5-11) were collected and freeze-dried.

The antitussive assessment of the above samples is shown in Table 5.

TABLE 5

| Sample | Dosage (g/kg) | N | Inhibition rate* (%) |
|---|---|---|---|
| 5-1 | 1 | 4 | 39 ± 9 |
|  | 0.5 | 4 | 32 ± 4 |
|  | 0.25 | 4 | 25 ± 4 |
| 5-2 | 1 | 4 | 89 ± 5 |
|  | 0.5 | 4 | 48 ± 3 |
|  | 0.25 | 4 | 35 ± 7 |
| 5-3 | 1.0 | 4 | 34 ± 7 |
| 5-4 | 1.0 | 8 | 41 ± 3 |
|  | 0.5 | 4 | 32 ± 12 |
|  | 0.25 | 4 | 17 ± 9 |
| 5-5 | 1.0 | 8 | 65 ± 5 |
|  | 0.5 | 4 | 64 ± 9 |
|  | 0.25 | 4 | 27 ± 1 |
| 5-6 | 1.0 | 4 | 41 ± 5 |
| 5-7 | 1.0 | 4 | 72 ± 8 |
| 5-8 | 1.0 | 4 | 42 ± 5 |
| 5-9 | 1.0 | 4 | 48 ± 8 |
|  | 0.5 | 4 | 44 ± 5 |
|  | 0.25 | 4 | 27 ± 3 |
| 5-10 | 1.0 | 4 | 55 ± 4 |
| 5-11 | 1 | 4 | 60 ± 7 |
|  | 0.5 | 4 | 55 ± 5 |
|  | 0.25 | 4 | 45 ± 6 |

*data are presented as means ± s.e. (N = 4 to 8)

The results in Table 5 show that after various processes of the crude extracts of *Cynanchum atratum*, the fractions, such as Samples 5-2, 5-5, 5-7, 5-9, 5-10 and 5-11, still show efficacy for reducing citric acid-induced coughs.

EXAMPLE 6

1500 g of dried *Cynanchum atratum* was extracted with water as in Example 1. The water extract containing 285 g dry powder was further loaded onto a reverse phase column packed with 5700 g HP20 resin in a ratio of 1 g dry basis of the extract/20 g resin. The column was first eluted with 45600 g water and then eluted with 95% ethanol. 45600 g 95% ethanol eluate was collected and concentrated approximately 50 times and then had water added to adjust a concentration of 10 mg/ml and then was concentrated 10 times. The concentrated solution was filtered by a filter paper (Whatman No. 2) to obtain the filtrate. The filtrate was then freeze-dried (Sample 6-1). The antitussive assessment of the above samples is shown in Table 6.

TABLE 6

| Sample | Dosage (g/kg) | Inhibition rate* (%) |
|---|---|---|
| 6-1 | 1.0 | 60 ± 11 |
|  | 0.5 | 58 ± 4 |
|  | 0.25 | 42 ± 12 |

*data are presented as means ± s.e. (N = 4)

The results in Table 6 show Sample 6-1 is active for reducing citric acid-induced coughs, even at 0.25 g/kg dosage.

EXAMPLE 7

2500 g of dried *Cynanchum atratum* was extracted with water as in Example 1. 40420 g water extract collected was further filtered by way of an ultrafiltration membrane with molecular weight cut off 1,000 (M12, speed: 50%, inlet P=20 psi). 36380 g of the filtrate was firstly collected and 36380 g water was added to the retentate to continue the ultrafiltration, repeating the process for 3 times. The retentate containing substances with molecular weight more than 1,000 dalton was collected, concentrated and freeze-dried as Sample 7-1.

The filtrate containing substances with molecular weight less than 1,000 dalton was collected and concentrated 3 times. The concentrated filtrate containing 420 g dry powder was then loaded onto a reverse phase column packed with 8400 g HP20 resin in a ratio of 1 g dry basis of the extract/20 g resin. The column was first eluted with 67200 g water and then eluted with 95% ethanol. 67200 g 95% ethanol eluate (Sample 7-2) was collected, concentrated and freeze-dried. 40 g dry powder of the ethanol eluate was added in 4000 g water as a concentration of 10 mg/mL. The solution was further partitioned with 4000 mL hexane for 3 times to collect the water fraction. The water fraction was subsequently filtered by a filter paper (Whatman No. 2) and the filtrate was freeze-dried as Sample 7-3.

The antitussive assessment of the above samples is shown in Table 7.

TABLE 7

| Sample | Dosage (g/kg) | Inhibition rate* (%) |
|---|---|---|
| 7-1 | 1.0 | 38 ± 4 |
| 7-2 | 1.0 | 71 ± 4 |
| 7-3 | 1.0 | 78 ± 4 |
|  | 0.5 | 52 ± 8 |
|  | 0.25 | 36 ± 6 |

*data are presented as means ± s.e. (N = 4)

The results in Table 7 show Sample 7-2 and 7-3 are active for reducing citric acid-induced coughs.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A pharmaceutical composition comprising an effective amount of an extract of a Radix *Cynanchi atrati* and a pharmaceutically acceptable carrier or excipient; wherein said extract is an eluate of said Radix *Cynanchi atrati* prepared by the steps of:
   extracting said Radix *Cynanchi atrati* with water, ethanol, ethyl acetate, hexane or a combination thereof to obtain a crude extract;
   loading said crude extract onto a reverse phase column;
   eluting said reverse phase column with water and an 80-95% ethanol solution sequentially to collect said eluate of said Radix *Cynanchi atrati*.

2. The pharmaceutical composition according to claim 1, wherein said crude extract of said Radix *Cynanchi atrati* is further filtered with an ultrafiltration membrane or a sieve.

3. The pharmaceutical composition according to claim 2, wherein said ultrafiltration membrane has a molecular weight cutoff of 1,000 dalton.

4. The pharmaceutical composition according to claim 1, wherein said extract of said Radix *Cynanchi atrati* is an antitussive agent.

5. The pharmaceutical composition as claimed in claim 1, wherein the extract of the Radix *Cynanchi atrati* is prepared by the steps of:
   extracting the Radix *Cynanchi atrati* with water, ethanol, ethyl acetate, hexane or a combination thereof to obtain the crude extract;
   filtering the crude extract with an ultrafiltration membrane with a molecular weight cut off of 1000 daltons to obtain a filtrate;
   loading the filtrate onto the reverse phase column; and
   eluting the reverse phase column with the water and the ethanol solution sequentially to collect an ethanol eluate;
   adding water to the ethanol eluate to obtain a concentrate of about 5-20 mg dry basis/ml;
   partitioning the concentrate with hexane to obtain a water fraction;
   concentrating the water fraction to obtain a concentrated water fraction; and
   filtering the concentrated water fraction with the ultrafiltration membrane to obtain the extract of the Radix *Cynanchi atrati*.

6. The pharmaceutical composition as claimed in claim 1, wherein the reverse phase column is packed with a styrene and divinylbenzene copolymer resin or a $C_{18}$-reverse phase silica gel.

7. The pharmaceutical composition as claimed in claim 6, wherein the reverse phase column is packed in a ratio of about 1 g dry basis of the crude extract/10 g to 120 g resin.

8. The pharmaceutical composition as claimed in claim 1, wherein the Radix *Cynanchi atrati* is *Cynanchum atratum* Bunge or *Cynanchum versicolor* Bunge.

9. A pharmaceutical composition for treating cough, comprising:
   an effective amount of a fractionated extract of the Radix *Cynanchi atrati* and a pharmaceutically acceptable carrier or excipient;
   wherein the fractionated extract of the Radix *Cynanchi atrati* is an eluate of a crude extract of the Radix *Cynanchi atrati* eluting from a reverse phase column chromatography with water and ethanol solution sequentially, which is prepared by the steps of:
   extracting the Radix *Cynanchi atrati* with water, ethanol or a combination thereof to obtain a crude extract;
   loading the crude extract onto a reverse phase column;
   eluting the reverse phase column with water and 80-95% ethanol solution sequentially to collect an ethanol eluate;
   concentrating the ethanol eluate to about 50 times to collect a concentrated ethanol eluate; adding water to the concentrated ethanol eluate to dilute the concentrated ethanol eluate to about 5-20 mg dry basis/ml and then concentrating to about 10 times to form a 10 times-concentrated eluate; and
   filtering the 10 times-concentrated eluate to obtain the fractionated extract of the Radix *Cynanchi atrati*.

10. The pharmaceutical composition as claimed in claim 9, wherein the reverse phase column is packed with a styrene and divinylbenzene copolymer resin or a $C_{18}$-reverse phase silica gel.

11. The pharmaceutical composition as claimed in claim 10, wherein the column is packed in a ratio of about 1 g dry basis of the crude extract/10 g to 120 g of the resin or gel.

12. The pharmaceutical composition as claimed in claim 9, wherein the Radix *Cynanchi atrati* is *Cynanchum atratum* Bunge or *Cynanchum versicolor* Bunge.

* * * * *